(12) United States Patent
Power et al.

(10) Patent No.: US 8,517,010 B2
(45) Date of Patent: Aug. 27, 2013

(54) NEBULISER SYSTEM

(75) Inventors: John Sylvester Power, Moycullen (IE); Conor Paul Duffy, Roscahill (IE); Niall Smith, Alloa (GB); Dermot Clancy, Manorhamilton (IE); Kiernan Hyland, Galway (IE)

(73) Assignee: Stamford Devices Limited, Galway (IE)

( * ) Notice: Subject to any disclaimer, the term of this patent is extended or adjusted under 35 U.S.C. 154(b) by 683 days.

(21) Appl. No.: 12/568,409

(22) Filed: Sep. 28, 2009

(65) Prior Publication Data

US 2010/0078013 A1 Apr. 1, 2010

Related U.S. Application Data

(60) Provisional application No. 61/100,494, filed on Sep. 26, 2008.

(51) Int. Cl.
*A61M 11/00* (2006.01)
(52) U.S. Cl.
USPC ............ 128/200.18; 128/200.14; 128/200.16; 128/202.21; 128/203.21; 141/330
(58) Field of Classification Search
USPC ............ 128/200.14–200.23, 203.15, 202.21; 128/203.21; 141/329, 330; 222/80–83
See application file for complete search history.

(56) References Cited

U.S. PATENT DOCUMENTS

| 6,085,740 | A | | 7/2000 | Yehuda et al. | |
| 6,152,327 | A | * | 11/2000 | Rhine et al. | 222/88 |

(Continued)

FOREIGN PATENT DOCUMENTS

| WO | WO-02/056950 | 7/2002 |
| WO | WO-03/059424 | 7/2003 |

OTHER PUBLICATIONS

International Search Report for PCT/IE2009/000068, mailed May 11, 2010, published as WO 2010035252.

(Continued)

*Primary Examiner* — Steven Douglas
(74) *Attorney, Agent, or Firm* — Choate, Hall & Stewart LLP; Andrea L. C. Robidoux; Daniel S. Matthews

(57) ABSTRACT

A nebulizer 1 particularly for home use includes a housing 2 having an aerosol generator 3 mounted therein. The housing is closed by a hinged cap 4 and has an outlet 5 through which aerosol generated by the generator 3 is delivered. A suitable connector such as a mouthpiece 6 may be connected to the outlet 5. The housing 2 has a receiver for receiving a nebule 8. The receiver includes a slot 7 which is sized and/or shaped to accommodate only a nebule 8 of predetermined shape and/or size. The nebulizer cap 4 has a nebule opening device which may be in the form of a puncture pin 10 projecting therefrom to pierce the nebule 8 when the cap is moved to the closed position. The pin 10 is hollow or splined to regulate flow from the nebule. The nebulizer 1 also has a switch device for enabling operation of the aerosol generator 3 when the nebule 8 is opened. The switch device comprises a microswitch 12 on the housing which is engageable by a trigger 13 on the cap 4 when the cap is moved to the closed position. Aerosol generated by the aerosol generator 3 is delivered into a chamber defined by the nebulizer housing 2. Air passes into the chamber through air inlets 30. The air entrains the aerosolized medicament and the entrained aerosolized medicament is delivered from the nebulizer through the outlet 5.

21 Claims, 13 Drawing Sheets

(56) References Cited

U.S. PATENT DOCUMENTS

| | | | |
|---|---|---|---|
| 6,637,430 B1 * | 10/2003 | Voges et al. | 128/200.14 |
| 6,971,549 B2 * | 12/2005 | Leifheit et al. | 222/83 |
| 7,198,044 B2 * | 4/2007 | Trueba | 128/200.16 |
| 7,600,511 B2 * | 10/2009 | Power et al. | 128/200.24 |
| 7,721,730 B2 * | 5/2010 | Hamano et al. | 128/200.14 |
| 8,196,573 B2 * | 6/2012 | Fink et al. | 128/200.14 |
| 8,291,902 B2 * | 10/2012 | Abrams | 128/203.21 |
| 2003/0150445 A1 * | 8/2003 | Power et al. | 128/200.14 |

OTHER PUBLICATIONS

Written Opinion for PCT/IE2009/000068, mailed May 11, 2010, published as WO 2010035252.

International Preliminary Report on Patentability for PCT/IE2009/000068, mailed Mar. 29, 2011, published as WO 2010035252.

* cited by examiner

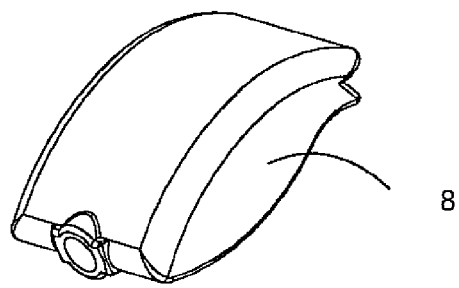
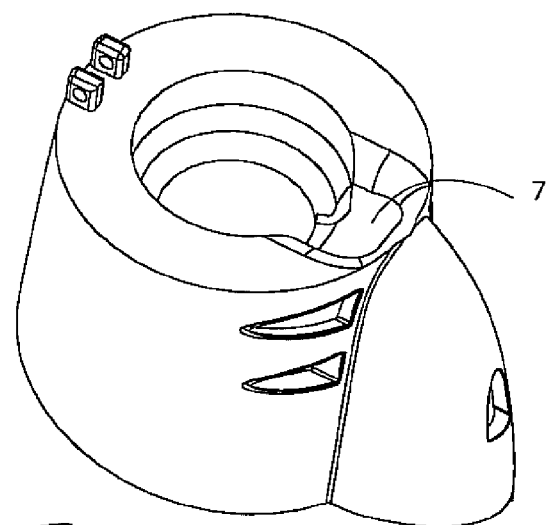
Fig. 9
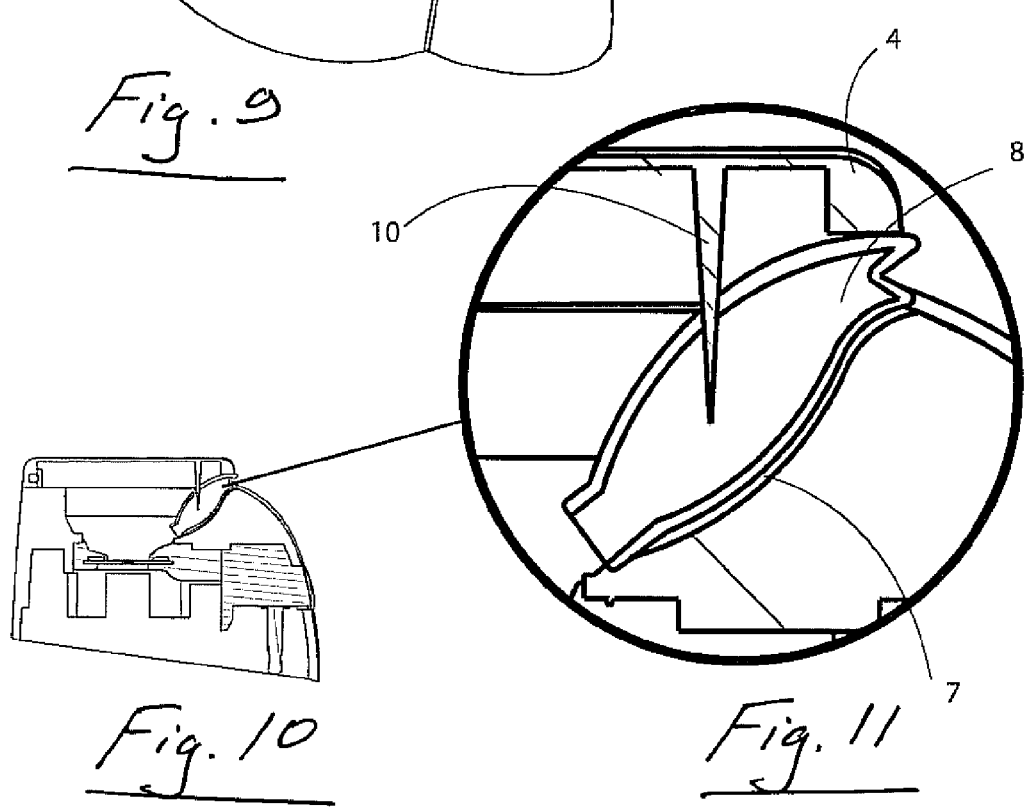
Fig. 10
Fig. 11

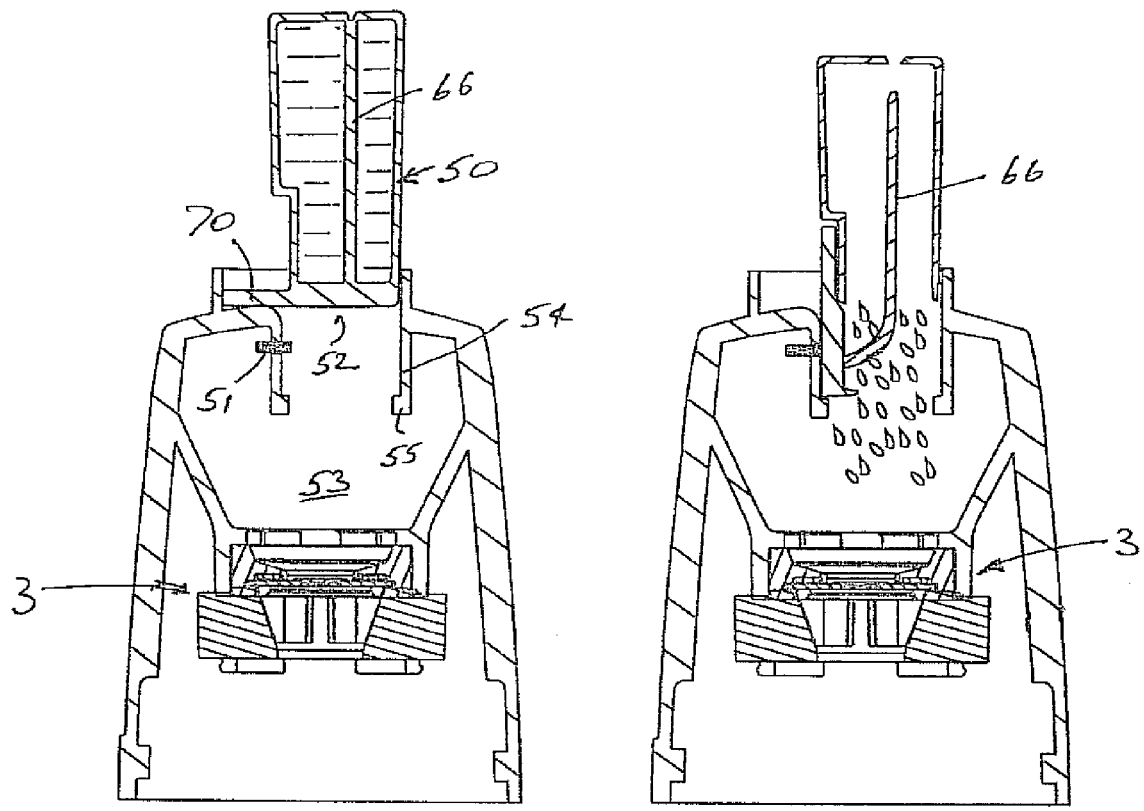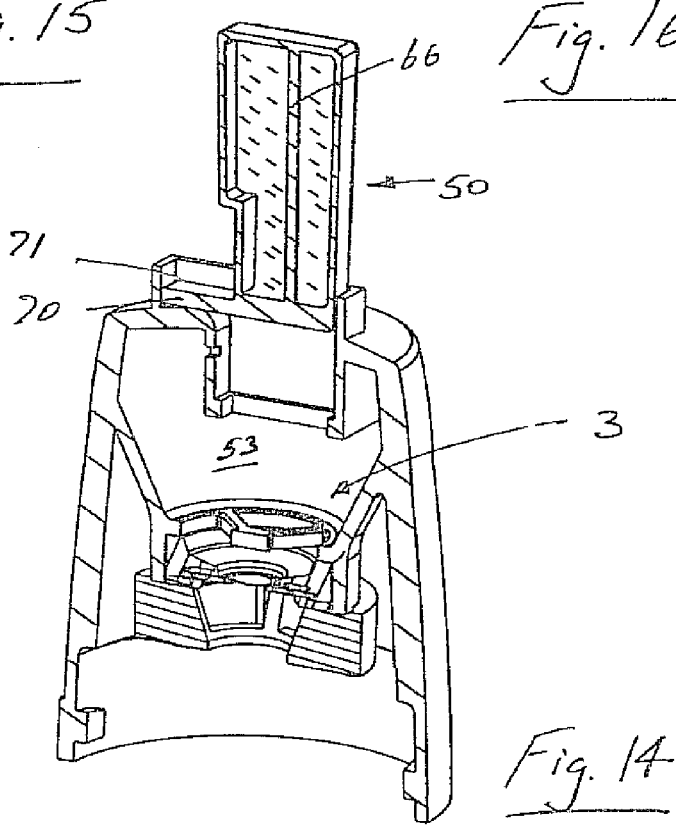

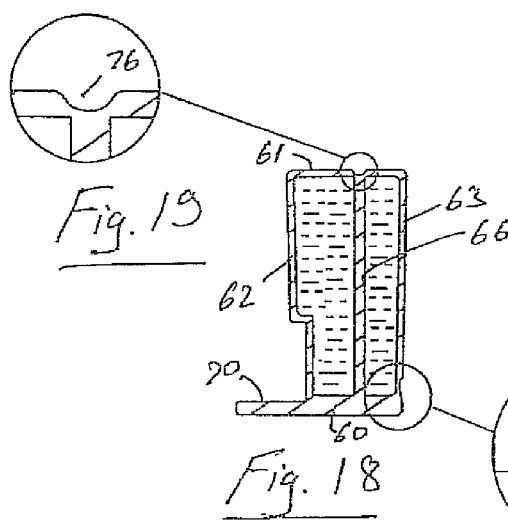
Fig. 19
Fig. 18
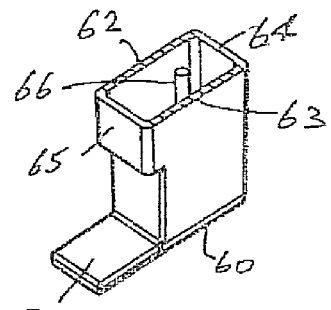
Fig. 17
Fig. 20
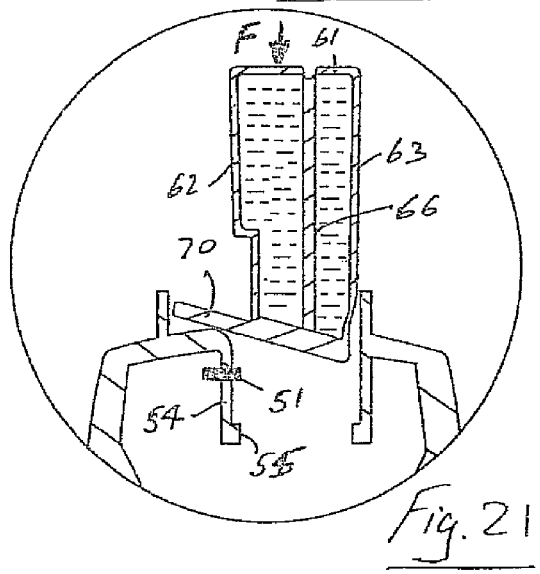
Fig. 21
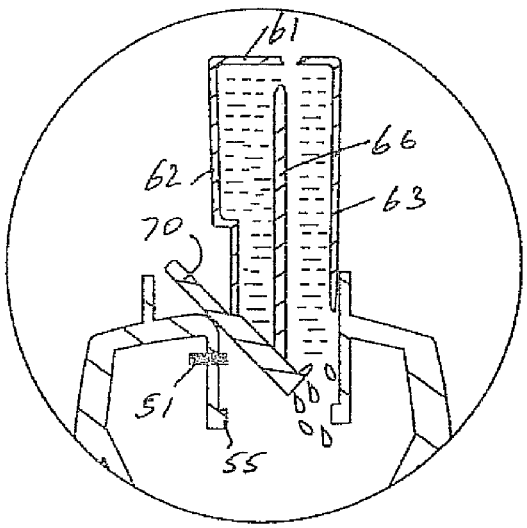
Fig. 22
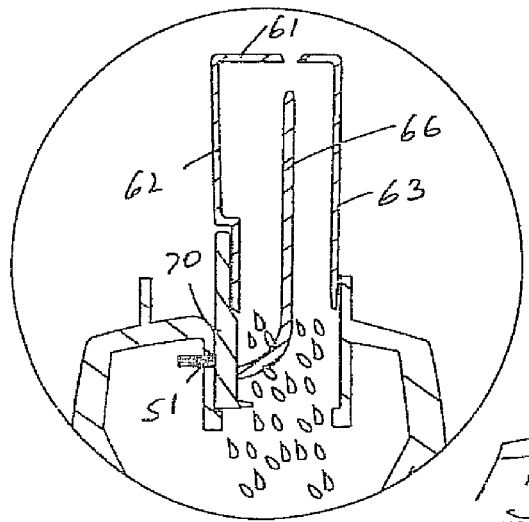
Fig. 23

NEBULISER SYSTEM

The present invention claims the benefit of U.S. Provisional Application No. 61/100,494 filed Sep. 26, 2008 the complete contents of which is incorporated herein by reference.

INTRODUCTION

Existing nebulisation systems for home use can be used with any drug.

In some instances this presents a risk that a patient or carer may inadvertently use an incorrect drug or an incorrect dosage of drug.

STATEMENTS OF INVENTION

In one aspect the invention provides a nebuliser comprising:
  a housing;
  an aerosol generator mounted in the housing; and
  a nebule receiver in the housing for receiving a nebule containing liquid to be aerosolised by the aerosol generator.

According to the invention there is provided a nebuliser comprising
  a housing;
  an aerosol generator mounted in the housing;
  a receiver for receiving a nebule containing a liquid to be aerosolised by the aerosol generator, a nebule being opened on insertion into the nebule receiver to deliver liquid from the nebule to the aerosol generator; and
  switch means for enabling operation of the aerosol generator on insertion and/or opening of a nebule.

The housing has an air inlet and an outlet for air with aerosol entrained therein. A mouthpiece can be attached to the housing outlet.

In one embodiment the nebuliser has an opening means for opening the nebule.

The opening means may comprise a nebule puncturing means.

The opening means may comprise means for cutting through a nebule.

The opening means may comprise means for tearing a nebule.

The opening means may comprise means for compressing a nebule.

The opening means may comprise means for squeezing a nebule.

In one case the nebuliser is closed by a cap.

The opening of the nebule may be triggered by the cap.

The activation of the switch means may be triggered by the cap.

In one embodiment the cap is movably mounted to the housing.

The cap may be hingedly mounted to the housing.

The cap may comprise a nebule opening means.

The nebule opening means may comprise a nebule puncturing means. The puncturing means may comprise a puncture pin projecting inwardly of the cap.

The puncture system may consist of a splined dagger. The splines would facilitate the ingress of air to the nebule to facilitate a drug stream to flow into the nebulizing system.

The switch means may be activated on movement of the cap from an open to a closed position.

In one embodiment the receiver is configured to facilitate opening of a nebule.

The receiver can comprise an opening in the housing to receive a nebule.

The receiver can comprise a skirt extending from the housing opening.

The skirt can comprise the switch means which is activated on insertion of a nebule.

In one embodiment the receiver is adapted to allow insertion of only a pre-determined nebule.

In one embodiment the receiver comprises a slot for a nebule, the slot being sized and/or shaped to accommodate a nebule of predetermined shape and/or size.

In another embodiment the nebuliser comprises a baffle means to elongate the path traveled by aerosol. The elongation of the flow path is assisted by increasing the breathing resistance by adjusting the size of the openings of the air vents. The efficiency of drug deposition is thereby enhanced as the aerosol is entrained from the generator to the mouth piece.

In one embodiment the nebuliser has air vent means and an air vent restrictor means to adjust the size of the air vent means.

In another aspect the invention provides a nebulisation kit comprising a nebuliser of the invention and at least one nebule or ampoule for use with the nebuliser. The nebule is operable from a closed configuration to an open configuration.

In one case the nebule comprises at least one zone of weakness which is fractured to open the nebule.

The nebule typically comprises a liquid outlet and a vent inlet. The liquid outlet and the vent inlet can be defined by zones of weakness in the nebule.

In one embodiment the nebule comprises a tab which, on insertion of the nebule into the receiver causes the liquid to be released from the nebule.

In one case the nebule comprises a top wall, a base and sidewall means extending between the base and the top, the tab forming an extension of the base.

The nebule may comprise an internal rib extending from the top to the base.

In one case the nebule comprises a first zone of weakness at a junction between the top wall and the internal rib. The nebule may also comprise a second zone of weakness at a junction between the base and the sidewall means.

In one case the tab is movable, on insertion of the nebule into the receiver to break the joint between the base wall and the sidewall. The movement of the tab may cause the joint between the internal rib and the top wall to break.

In a further aspect the invention provides a nebule comprising a top wall, a base wall, sidewall means extending between the base and a tab extending from the base wall, the tab being movable to fracture the joint between the base wall and the sidewall for release of liquid from the nebule.

In one case the nebule comprises an internal rib extending between the base wall and the top wall.

The nebule can have a zone of weakness in the top wall at a joint between the top wall and the internal rib, movement of the tab causing the joint between the rib and the top wall to fracture.

In a further aspect the invention provides a nebuliser comprising:—
  a housing;
  an aerosol generator mounted in the housing; and
  a baffle in the housing to elongate the path traveled by aerosol generated by the aerosol generator.

The housing has an air inlet and an outlet for air with aerosol entrained therein.

There may be a mouthpiece attached to the housing outlet.

In one case the baffle is located in the housing between the inlet and the outlet.

The elongation of the flow path may be assisted by increasing the breathing resistance by adjusting the size of the openings of the air vents. The efficiency of drug deposition is thereby enhanced as the aerosol is entrained from the generator to the mouth piece.

In another aspect the invention provides a nebuliser comprising:—
a housing;
an aerosol generator mounted in the housing;
the housing having an air vent means; and
an adjustable restrictor to adjust the size of the opening defined by the air vent means.

The housing has an outlet for air with aerosol entrained therein.

There may be a mouthpiece attached to the housing outlet.

In one case the nebuliser comprises a baffle or auxiliary wall within the housing to elongate the aerosol flow path.

The auxiliary wall may be located between the air inlet and the aerosol outlet.

In one embodiment the nebuliser comprises a baffle or auxiliary wall to elongate the aerosol flow path. This increases the efficiency of drug deposition.

An advantageous feature is the matching of a particular drug contained within a pre specified nebule shape than can only be used in conjunction with the nebuliser design which is designed to nebulise the drug for a predetermined disease treatment. Putting the particular drug into a different nebuliser would not have the desired clinical effect. Putting a different drug into the same nebuliser would also not have the same clinical effect.

The nebuliser has opening means for opening the nebule to allow delivery of liquid from the nebule to the aerosol generator. The nebuliser also has switch means for enabling operation of the aerosol generator when the nebule is opened.

The closing cap may aid the egress of drug from the vial by a cutting, tearing, and/or a squeezing or compressing motion.

In one embodiment the switch means is activated on movement of the cap from an open to a closed position to facilitate activation of the aerosol generator to generate the aerosol Preferably the receiver is adapted to allow insertion of only a pre-determined nebule. The receiver may comprise a slot for a nebule, the slot being sized and/or shaped to accommodate a nebule of predetermined geometrical shape and/or size.

In one embodiment the nebuliser comprises baffle means to elongate the path traveled by aerosol from the generator to the patient. This causes the aerosol to be entrained thus facilitating a greater amount of the aersolised drug to be delivered to the patient.

In another aspect the nebuliser has air vent means and an air vent restrictor means to adjust the size of the air vent means. This has the advantage of adjusting the breathing resistance of the nebulizer to suit different patient groups, for example a large elderly person would have a different breathing profile to a child.

BRIEF DESCRIPTION OF THE DRAWINGS

The invention will be more clearly understood from the following description thereof given by way of example only with reference to the accompanying drawings, in which:—

FIGS. 6 to 11 are views of part of the nebuliser of FIGS. 1 to 4 in different configurations;

FIG. 14 is an isometric partially cut-away view of another nebuliser according to the invention with a sealed nebule according to the invention positioned on top of the nebuliser ready for opening;

FIG. 15 is a cross sectional view of the nebuliser and nebule of FIG. 14;

FIG. 16 is a cross sectional view of the nebuliser and nebule pushed into the nebuliser, thus opening the nebule and allowing the escapement of the nebule contents (which may include a drug) which egresses to the aerosol generator;

FIG. 17 is an isometric view of a nebule according to the invention with a top wall removed;

FIG. 18 is a cross sectional view of the closed nebule;

FIGS. 19 and 20 are enlarged cross sectional views of details of the nebule of FIG. 18; and FIGS. 21 to 23 are cross sectional views illustrating the opening of the nebule.

DETAILED DESCRIPTION

Figure 1:
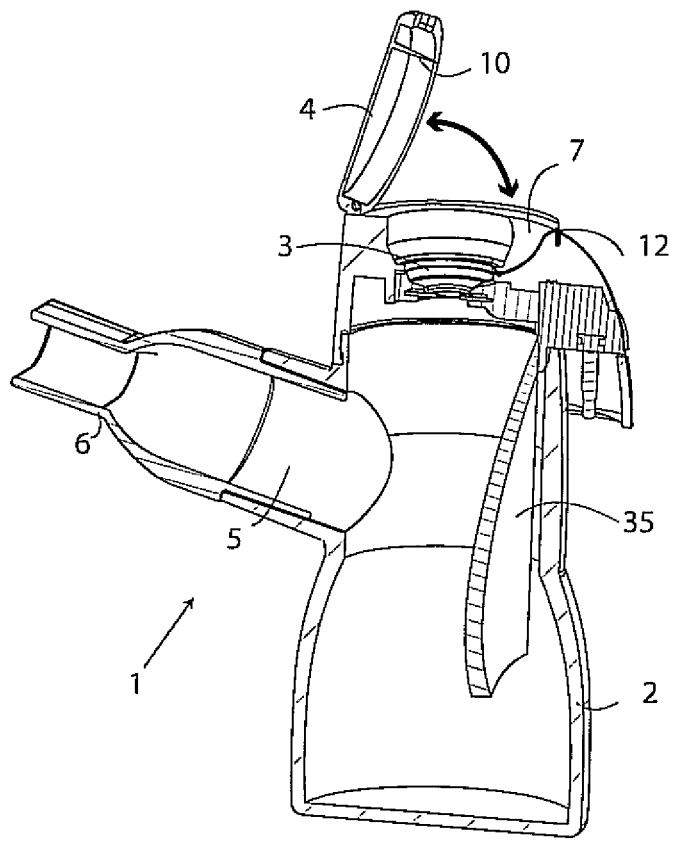
FIG. 1 is a cross sectional view of a nebuliser according to the invention in one configuration.
Figure 2:
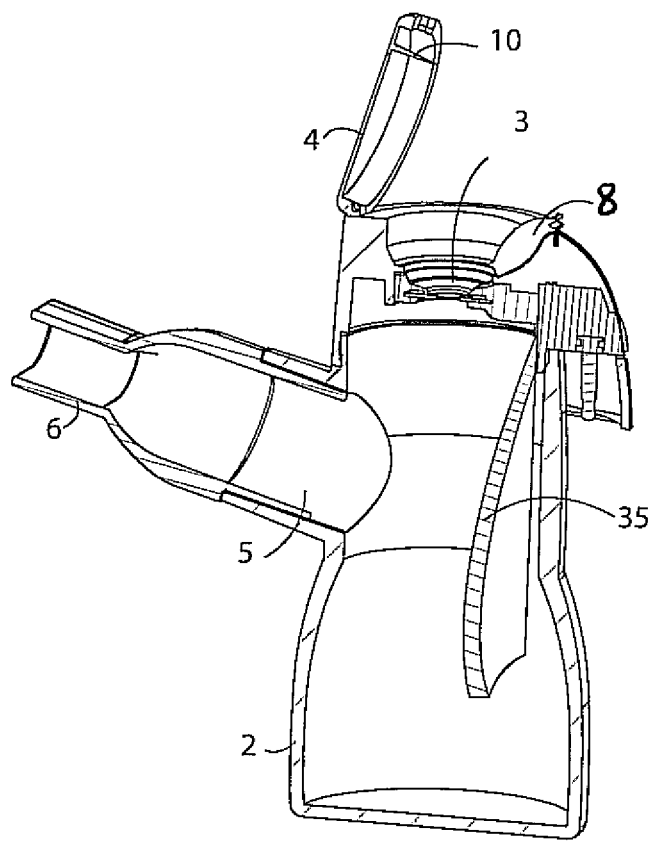
FIG. 2 is a cross sectional view of the nebuliser of FIG. 1 with a nebule in position.
Figure 3:
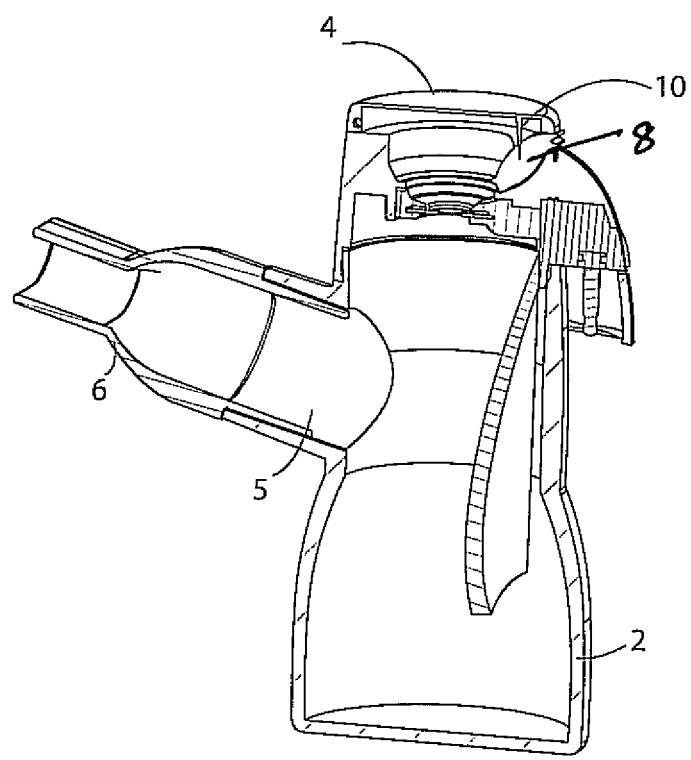
FIG. 3 is a cross sectional view of the nebuliser in another configuration in which the nebule is punctured.
Figure 4:
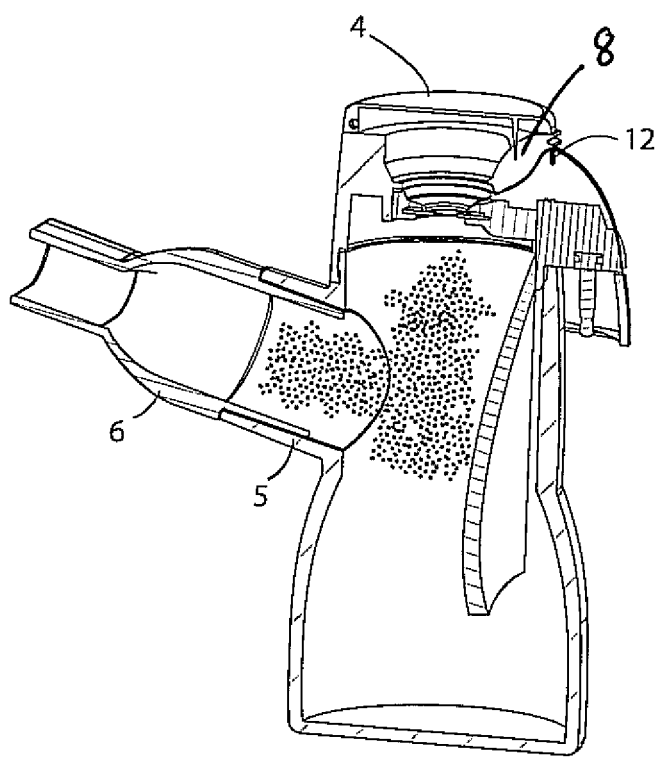
FIG. 4 is a cross sectional view of the nebuliser in the configuration of FIG. 3 with aerosol generated.
Figure 5:
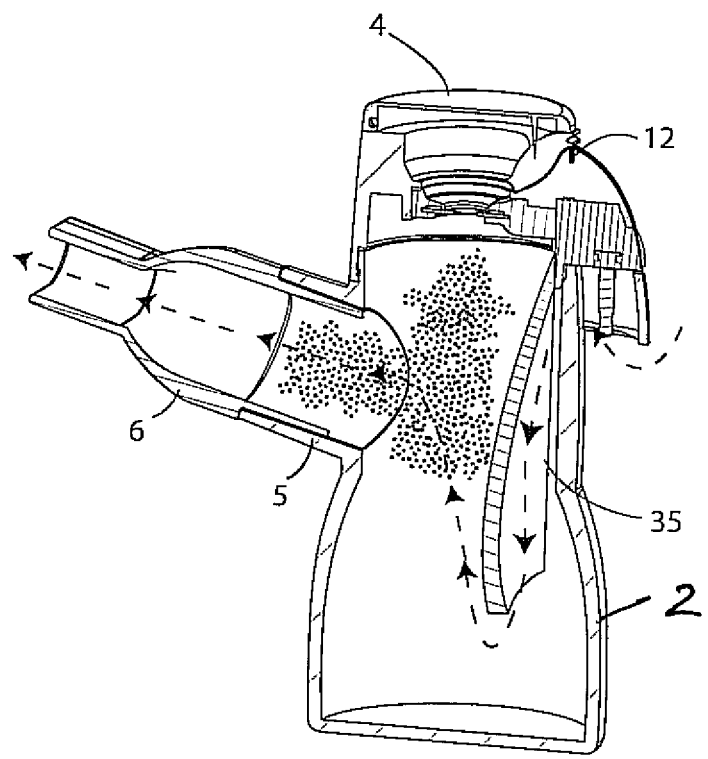
FIG. 5 is a cross sectional view similar to FIG. 4 illustrating the flow path.
Figure 6:
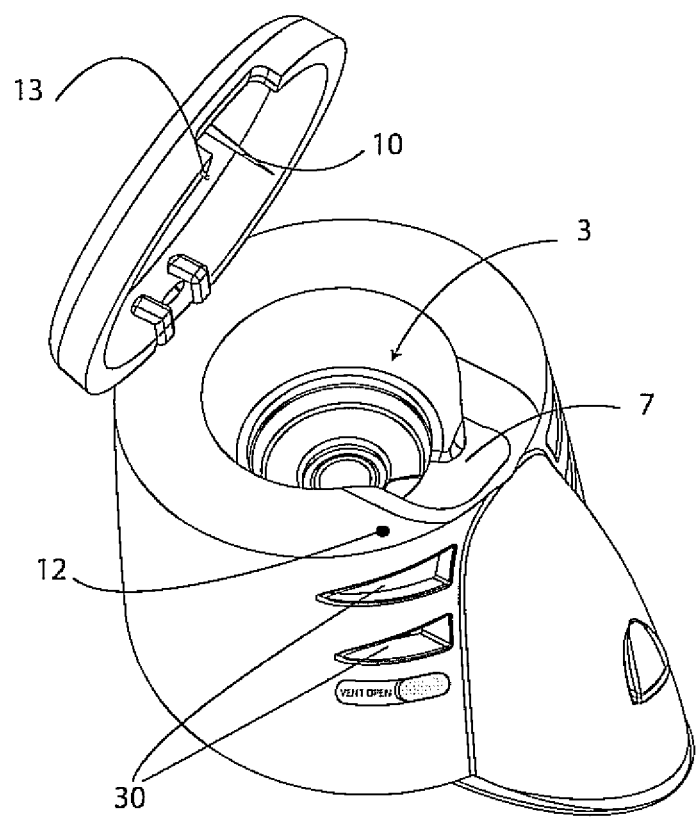
Figure 7:
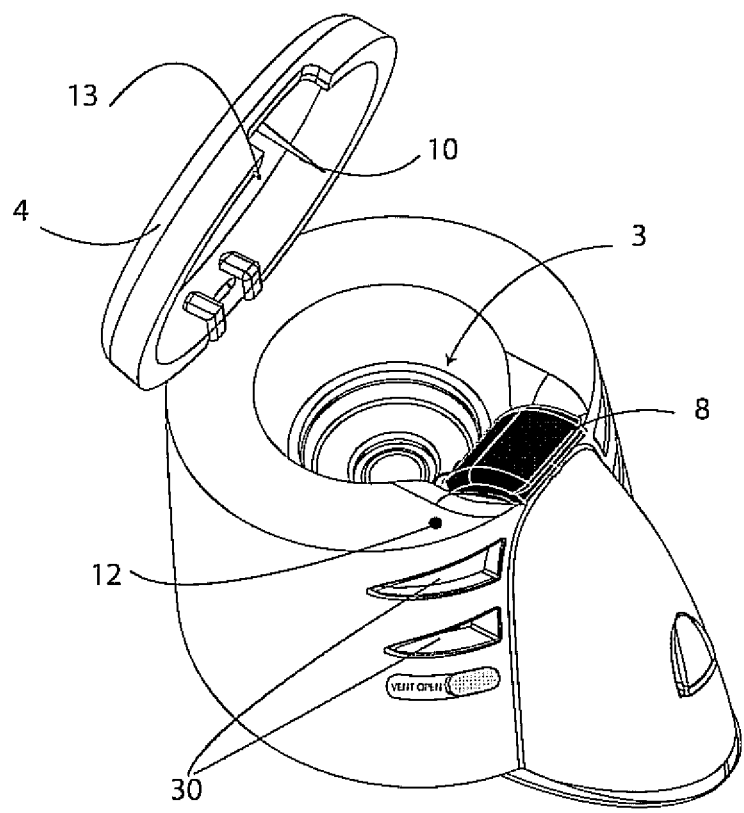
Figure 8:
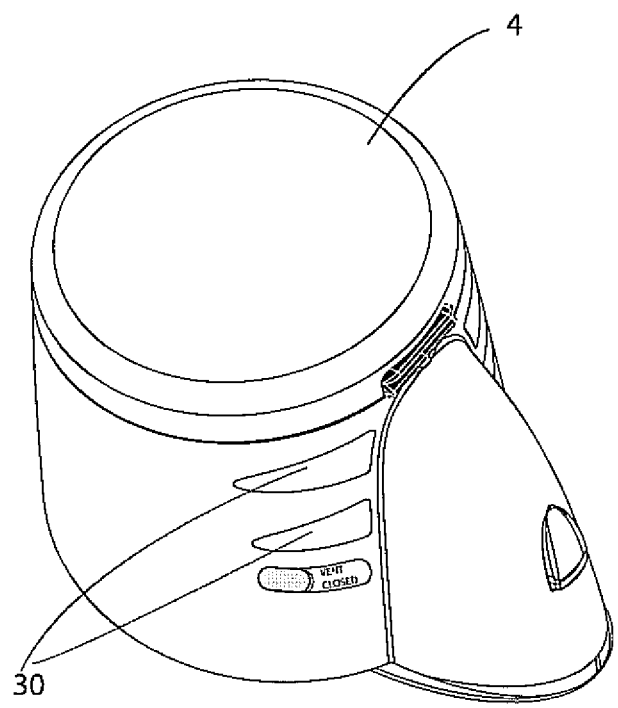

Referring to the drawings and initially to FIGS. 1 to 11 thereof there is illustrated a nebuliser 1 according to the invention which comprises a housing 2 having an aerosol generator 3 mounted therein. The housing is closed by a hinged cap 4 and has an inlet and an outlet 5 through which aerosol generated by the generator 3 is delivered. A suitable connector such as a mouthpiece 6 may be connected to the outlet 5. The nebuliser may be used on an outpatient basis and on non ventilated patients and is particularly suited for home use.

The housing 2 has a receiver for receiving a nebule 8. The receiver comprises a slot 7 which is sized and/or shaped to accommodate only a nebule 8 of predetermined shape and/or size.

The nebuliser cap 4 has a nebule opening means which in this case is in the form of a puncture pin 10 projecting therefrom to pierce the nebule 8 when the cap is moved to the closed position. The pin 10 is hollow or splined to regulate flow from the nebule. Making the pin hollow or splined facilitates air ingress to the nebule thus allowing the drug to be released into the nebuliser.

The cap, on closing may alternatively or additionally apply a compressive load on the nebule to aid the egress of drug from the nebule.

The nebuliser 1 also has a switch means for enabling operation of the aerosol generator 3 when the nebule 8 is opened. The switch means in this case comprises a micro-switch 12 on the housing which is engageable by a trigger 13 on the cap 4 when the cap is moved to the closed position.

In the invention the nebuliser has a hinged lid with a nebule-specific slot. Closing of the lid will enable drug release from the nebule. The closing of the lid will also electronically indicate to the nebuliser that the correct nebule is in correct position and that nebulisation can commence.

Aerosol generated by the aerosol generator 3 is delivered into a chamber defined by the nebuliser housing 2. Air passes into the chamber through air inlets 30. The air extrains the aerosolised medicament and the entrained aerosolised medicament is delivered from the nebuliser through the outlet 5. The vent openings 30 are adjustable to vary the breathing resistance. Different patients have different resistances and these can be adjusted to suit their breathing pattern. For example longer and slower breaths increases the drug intake.

A baffle system such as an internal or auxiliary wall 35 within the housing chamber 2 may be provided. The wall 35 is interposed between an air inlet 30 and the outlet 5 and forces air to flow towards the base of the housing 2 so that it entrains the aerosol generated. This elongates the distance traveled or uninterrupted pathway by aerosol from generation at 3 to the mouthpiece 6. This has been shown to increase the efficiency of the system by entraining more aerosol to be conveyed to the mouthpiece and patient.

Figure 12:
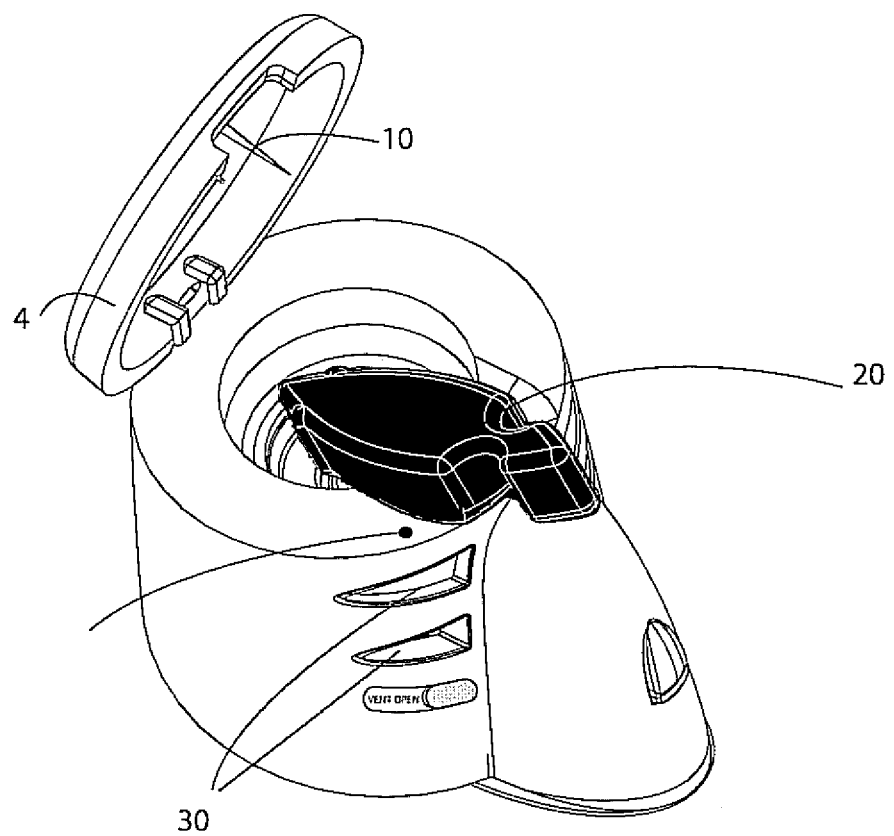
FIGS. 12 and 13 are views similar to FIGS. 7 and 8 of a nebuliser with an alternative nebule.
Figure 13:
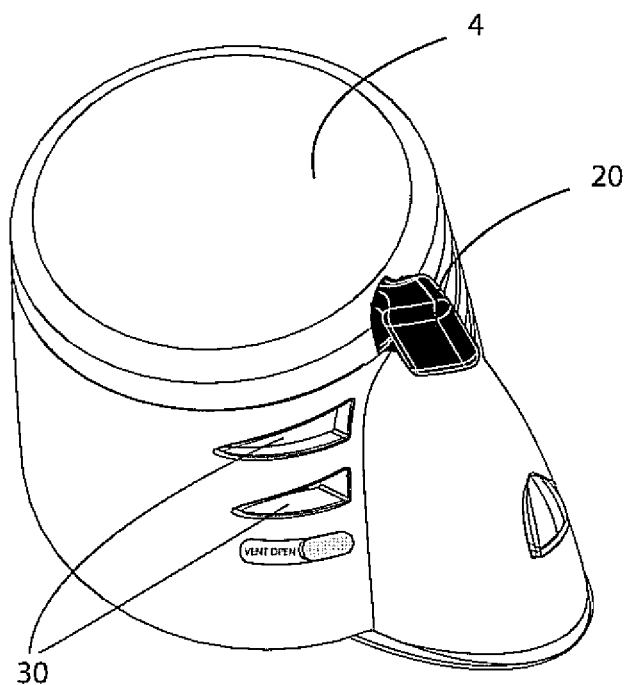

Referring to FIGS. 12 and 13, there is illustrated part of another nebuliser according to the invention in which parts similar to those described with reference to FIGS. 1 to 11 are assigned the same reference numerals. In this case a nebule 20 is of a different size and shape to the nebule 8 used in the nebuliser of FIGS. 1 to 11.

FIGS. 14 to 16 illustrate a similar aerosolising system to those described above with like parts being assigned the same reference numerals. The nebuliser system uses a different nebule 50 which is illustrated in FIGS. 17 to 23.

In this case, the action of depressing the nebule 50 into the aerosol generator causes the nebule 50 to tear open in a controlled manner and release the contents of the nebule (which may include drug) {expect it always include a drug} to the aerosol generator and at the same time depressing a microswitch 51 to close the electrical circuit to cause aersolisation to occur. The micro switch 51 may be engaged by the drug nebule 50. This switch 51 is activated by the nebule 50 and the switch 51 activates the generation of aerosol as the nebule is depressed into position.

The nebuliser in this case comprises a top opening 52 leading to a chamber 53 above the aerosol generator 3. A skirt 54 extends downwardly from the top opening 52. The switch 51 is provided on the skirt 54. The skirt 54 has an inturned lip 55 near the lower end thereof.

In more detail, the nebule or ampoule 50 comprises a base wall 60, a top wall 61 and side wall means extending between the base wall 60 and the top wall 61. In this case the nebule 50 is of generally rectilinear shape in transverse cross section and comprises side walls 62, 63 and end walls 64, 65. The nebule 50 also has an internal rib 66 which extends from the base wall 60 and is engagable in a receiver slot 71 on top of the nebuliser.

The nebule 50 has means to encourage localised fracturing or separation to facilitate opening of the nebule for release of the contents. In this embodiment the nebule has two zones of weakness which may be provided by a local thinning of the walls of the nebuliser. A first zone of weakness 75 is provided between the bottom of the side wall 64 and the base wall 60 opposite to the tab 70. A second zone of weakness 76 is provided between the top of the internal rib 66 and the top wall 61. In use, when a downwards force F is applied to the top of the nebule 50 the tab 70 is initially held in the slot 71. As further force is applied the zones of weakness 75, 76 cause parts of the nebule to fracture or separate. The second zone 76 causes the rib 66 to separate from the top wall 61 and thus define a hole 80 which defines an air inlet/vent. The first zone 75 causes the base wall 60 to fracture or separate from the side wall 64 thereby defining an outlet hole 81 through which the contents of the nebule 50 pass to be delivered into the chamber 53 which leads the liquid to the aerosol generator 3. Because the switch 51 is activated by the tab 70, as illustrated, a signal is provided to activate the aerosol generator.

It will be appreciated that at least some of the features described herein may be used in association with nebules and/or nebulisers for ventilator circuits. At least some of the features described herein may be used with nebules and/nebulisers for laparoscopy applications as described in our US2008/0243050A1, the entire contents of which are incorporated herein by reference.

The nebuliser (or aerosol generator) 3, has a vibratable member which is vibrated at ultrasonic frequencies to produce liquid droplets. Some specific, non-limiting examples of technologies for producing fine liquid droplets is by supplying liquid to an aperture plate having a plurality of tapered apertures extending between a first surface and a second surface thereof and vibrating the aperture plate to eject liquid droplets through the apertures. Such technologies are described generally in U.S. Pat. Nos. 5,164,740; 5,938,117; 5,586,550; 5,758,637; 6,755,189, 6,540,154, 6,926,208, 7,174,888, 6,546,927, 6,085,740, and US2005/021766A, the complete disclosures of which are incorporated herein by reference. However, it should be appreciated that the present invention is not limited for use only with such devices.

In use, the liquid to be aerosolised is received at the first surface, and the aerosol generator 3 generates the aerosolised liquid at the second surface by ejecting droplets of the liquid upon vibration of the vibratable member. The apertures in the vibratable member are sized to aerosolise the liquid by ejecting droplets of the liquid such that the majority of the droplets by mass have a size of less than 5 micrometers.

In one case the aerosol generator 3 comprises a vibratable member, a piezoelectric element and a washer, which are sealed within a silicone overmould and secured in place within the housing a retaining ring. The vibratable member has a plurality of tapered apertures extending between a first surface and a second surface thereof.

The first surface of the vibratable member, which in use faces upwardly, receives the liquid from the nebule 50 and the aerosolised liquid, is generated at the second surface of the vibratable member by ejecting droplets of liquid upon vibration of the member. In use, the second surface faces downwardly. In one case, the apertures in the vibratable member may be sized to produce an aerosol in which the majority of the droplets by weight have a size of less than 5 micrometers. The vibratable member could be non-planar, and may be dome-shaped in geometry.

Any suitable medicament, therapeutic agent, active substance or pharmaceutically active compound than can be nebulised may be employed. {Comment—we do not expect this to be used to deliver a humidifying agent—only drug unless we are covering the potential for use in the laparoscopy application} also act to deliver any agent presented in an aqueous drug solution. {These therapeutic agents could also act as humidifying substances in their own right.}

The system facilitates delivery in aerosol form of, for example, bronchodilators, including β-agonists, muscarinic antagonists, epinephrine; surfactants; pain-relief medications including anaesthetics; migraine therapies; anti-infectives; anti-inflammatories, steroids, including corticostroids; chemotherapeutic agents; mucolytics; vasodilators; vaccines and hormones. In addition substances classified as anti-thrombogenic agents, anti-proliferative agents, monoclonal antibodies, anti-neoplastic agents, anti-mitotic agents, anti-sense agents, anti-microbial agents, nitric oxide donors, anti-coagulants, growth factors, translational promoter, inhibitors of heat shock proteins, biomolecules including proteins, polypeptides and proteins, oligonucleotides, oligoproteins, siRNA, anti-sense DNA and RNA, ribozymes, genes, viral vectors, plasmids, liposomes, angiogenic factors, hormones, nucleotides, amino acids, sugars, lipids, serine proteases, anti-adhesion agents including but not limited to hyaluronic acid, biodegradable barrier agents may also be suitable.

The medicament may for example, comprise long-acting beta-adrenoceptor agonists such as salmeterol and formoterol or short-acting beta-adrenoceptor agonists such as albuterol.

The medicament may be a long-acting muscarinic antagonists such as tiotropium (Spiriva) or short-acting muscarinic antagonists such as ipratropium (Atrovent).

Typical anti-infectives include antibiotics such as an aminoglycoside, a tetracycline, a fluoroquinolone; anti-microbials such as a cephalosporin; and anti-fungals. Examples of antibiotics include anti-gram-positive agents such as macrolides, e.g. erythromycin, clarithromycin, azithromycin, and glycopeptides, e.g. vancomycin and teicoplanin, as well as any other anti-gram-positive agent capable of being dissolved or suspended and employed as a suitable aerosol, e.g. oxazoldinone, quinupristin/dalfopristen, etc. Antibiotics useful as anti-gram-negative agents may include aminoglycosides, e.g. gentamicin, tobramycin, amikacin, streptomycin, netilmicin, quinolones, e.g. ciprofloxacin, ofloxacin, levofloxacin, tetracyclines, e.g. oxytetracycline, dioxycycline, minocycline, and cotrimoxazole, as well as any other anti-gram-negative agents capable of being dissolved or suspended and employed as a suitable aerosol.

Anti-inflammatories may be of the steroidal such as budesonide or ciclesonide, non-steroidal, such as sodium cromoglycate or biological type.

Typical local anaesthetics are, for example, Ropivacaine, Bupivacaine, levobupivacaine, and Lidocaine.

Chemotherapeutic agents may be alkylating agents, antimetabolites, anthracyclines, plant alkaloids, topoisomerase inhibitors, nitrosoureas, mitotic inhibitors, monoclonal antibodies, tyrosine kinase inhibitors, hormone therapies including corticosteroids, cancer vaccines, anti-estrogens, aromatase inhibitors, anti-androgens, anti-angiogenic agents and other anti-tumour agents.

Surfactant medications (sometimes referred to herein as "surfactants") are protein-lipid compositions, e.g. phospholipids, that are produced naturally in the body and are essential to the lungs' ability to absorb oxygen. They facilitate respiration by continually modifying surface tension of the fluid normally present within the air sacs, or alveoli, that tube the inside of the lungs. In the absence of sufficient surfactant, these air sacs tend to collapse, and, as a result, the lungs do not absorb sufficient oxygen. Insufficient surfactant in the lungs results in a variety of respiratory illnesses in both animals and humans. Since most of these surfactant medications are animal-based, the current supply is limited, and although synthetic surfactants are available, their manufacture is both inexact and expensive. In addition, the surfactant medications are typically high in viscosity and are difficult to deliver to the patient's respiratory system. The increased efficiency of the pressure-assisted breathing system of the present invention, and the smaller amount of medicament required for a treatment according to the present invention, can be a substantial advantage when such scarce and expensive medicaments are employed. The combination of surfactant with other medicaments to improve distribution in the lung and body is also possible. Surfactants also possess the capacity to act as anti-adhesion agents.

The invention provides a closed-cup home care nebuliser. This system ensures that only the required nebule (and therefore drug) can be used with this high-efficiency system. The nebuliser chamber is designed to maximise efficiency of drug delivery. In use, fewer steps are involved for a patient in using the system. This is particularly advantageous for older people.

An adjustable air vent restrictor (hydrophobic media, or a mechanical slider occlusion system may be incorporated into nebuliser vent holes 30 to vary the air resistance through the system to condition patients breathing. Patients of differing ages or ailment conditions would have a different breathing pattern need. The breathing pattern is influenced by the inhalation and exhalation resistance when using the nebuliser. This can be controlled by changing the area of the vent holes 30. Closing these more increases the resistance and opening these more reduces the resistance. The air vent restrictor can be used to condition a patients breathing pattern. This helps to create a longer and slower breathing pattern to maximise drug delivery.

The invention is not limited to the embodiments hereinbefore described which may be varied in detail.

The invention claimed is:

1. A nebuliser comprising:— a housing;

an aerosol generator mounted in the housing;

a receiver for receiving a nebule containing a liquid to be aerosolised by the aerosol generator;

a cap for closing the nebuliser;

the cap comprising a nebule opener; and a switch for enabling operation of the aerosol generator on insertion and/or opening of a nebule.

2. A nebuliser as claimed in claim 1 wherein the housing has an air inlet and an outlet for air with aerosol entrained therein.

3. A nebuliser as claimed in claim 2 comprising a mouthpiece attached to the housing outlet.

4. A nebuliser as claimed in claim 1 wherein the nebule opener comprises a nebule puncturer.

5. A nebuliser as claimed in claim 1 wherein the nebule opener comprises a nebule cutter.

6. A nebuliser as claimed in claim 1 wherein the nebule opener comprises a nebule tearer.

7. A nebuliser as claimed in claim 1 wherein the nebule opener comprises a nebule compressor.

8. A nebuliser as claimed in any claim 1 wherein the nebule opener comprises a nebule squeezer.

9. A nebuliser as claimed in claim 1 wherein the activation of the switch is triggered by the cap.

10. A nebuliser as claimed in claim 1 wherein the cap is movably mounted to the housing.

11. A nebuliser as claimed in claim 10 wherein the cap is hingedly mounted to the housing.

12. A nebuliser as claimed in claim 4 wherein the puncturer comprises a puncture pin projecting inwardly of the cap.

13. A nebuliser as claimed in claim 10 wherein the switch means is activated on movement of the cap from an open to a closed position.

14. A nebuliser as claimed in claim 1 wherein the receiver is configured to facilitate opening of a nebule.

15. A nebuliser as claimed in claim 14 wherein the receiver comprises an opening in the housing to receive a nebule.

16. A nebuliser as claimed in claim 15 wherein the receiver comprises a skirt extending from the housing opening.

17. A nebuliser as claimed in claim 16 wherein the skirt comprises the switch means which is activated on insertion of a nebule.

18. A nebuliser as claimed in claim 1 wherein the receiver is adapted to allow insertion of only a pre-determined nebule.

19. A nebuliser as claimed in claim 1 wherein the receiver comprises a slot for a nebule, the slot being sized and/or shaped to accommodate a nebule of predetermined shape and/or size.

20. A nebuliser as claimed in claim 1 comprising a baffle to elongate the path traveled by aerosol.

21. A nebuliser as claimed in claim 1 wherein the nebuliser comprises an air vent and an air vent restrictor to adjust the size of the air vent.

* * * * *

UNITED STATES PATENT AND TRADEMARK OFFICE
CERTIFICATE OF CORRECTION

PATENT NO. : 8,517,010 B2  
APPLICATION NO. : 12/568409  
DATED : August 27, 2013  
INVENTOR(S) : John S. Power et al.

Page 1 of 1

It is certified that error appears in the above-identified patent and that said Letters Patent is hereby corrected as shown below:

On the title page, item [75] under "Inventors", delete "Kiernan Hyland" and replace with – Kieran Hyland Signed and Sealed this
Twenty-seventh Day of May, 2014

Michelle K. Lee
*Deputy Director of the United States Patent and Trademark Office*